(12) United States Patent
Decker et al.

(10) Patent No.: US 12,727,896 B2
(45) Date of Patent: Sep. 8, 2026

(54) MAGNETICALLY DRIVEN CROSSING TOOLS FOR ARTERIAL AND VENOUS OCCLUSIONS

(71) Applicant: KONINKLIJKE PHILIPS N.V., Eindhoven (NL)

(72) Inventors: Cedar Decker, Albertville, MN (US); Mitchell Erickson, Crystal, MN (US); Kerianne Steucke, Maple Grove, MN (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 314 days.

(21) Appl. No.: 18/569,020

(22) PCT Filed: Jun. 3, 2022

(86) PCT No.: PCT/EP2022/065265
§ 371 (c)(1),
(2) Date: Dec. 11, 2023

(87) PCT Pub. No.: WO2022/263213
PCT Pub. Date: Dec. 22, 2022

(65) Prior Publication Data

US 2024/0277359 A1 Aug. 22, 2024

Related U.S. Application Data

(60) Provisional application No. 63/211,016, filed on Jun. 16, 2021.

(51) Int. Cl.

| | |
|---|---|
| ***A61B 17/22*** | (2006.01) |
| ***A61B 17/00*** | (2006.01) |
| ***A61B 90/00*** | (2016.01) |

(52) U.S. Cl.
CPC ........ *A61B 17/22* (2013.01); *A61B 17/00234* (2013.01); *A61B 90/39* (2016.02);
(Continued)

(58) Field of Classification Search
CPC .............. A61B 17/00234; A61B 17/22; A61B 2017/00137; A61B 2017/00292;
(Continued)

(56) References Cited

U.S. PATENT DOCUMENTS 5,269,759 A * 12/1993 Hernandez ............ A61M 25/09
604/529
5,431,640 A * 7/1995 Gabriel ............... A61J 15/0007
600/12
(Continued)

FOREIGN PATENT DOCUMENTS

| | | |
|---|---|---|
| EP | 1289593 A1 | 3/2003 |
| WO | 2001093939 A1 | 12/2001 |

(Continued)

OTHER PUBLICATIONS

International Search Report and Written Opinion Dated Nov. 28, 2022 For International Application No. PCT/EP2022/065265 Filed Jun. 3, 2022.

*Primary Examiner* — Ryan J. Severson

(57) ABSTRACT

A guidewire insertion device (10) includes a first guidewire (12) including an electromagnetic tip (14); a second guidewire (16) including a magnetic tip (18); and a controller (33) configured to modulate a force of the electromagnetic tip of the first guidewire to control movement of the magnetic tip of the second guidewire.

17 Claims, 5 Drawing Sheets

(52) U.S. Cl.
CPC ............... *A61B 2017/00137* (2013.01); *A61B 2017/00292* (2013.01); *A61B 2017/00778* (2013.01); *A61B 2017/00862* (2013.01); *A61B 2017/00867* (2013.01); *A61B 2017/00876* (2013.01); *A61B 2017/00946* (2013.01); *A61B 2017/22044* (2013.01); *A61B 2017/22045* (2013.01); *A61B 2017/22094* (2013.01); *A61B 2090/3966* (2016.02)

(58) Field of Classification Search
CPC .......... A61B 2017/00778; A61B 2017/00862; A61B 2017/00867; A61B 2017/00876; A61B 2017/00946; A61B 2017/22038; A61B 2017/22042; A61B 2017/22044; A61B 2017/22045; A61B 2017/22094; A61B 90/39; A61B 2090/3966; A61M 25/0127; A61M 25/09041; A61M 2025/09133; A61M 2025/09175; A61M 2025/09183
See application file for complete search history.

(56) References Cited

U.S. PATENT DOCUMENTS

| | | | | | |
|---|---|---|---|---|---|
| 5,464,023 | A * | 11/1995 | Viera | A61M 25/0169 | 600/585 |
| 5,606,980 | A | 3/1997 | Calhoun | | |
| 5,623,943 | A * | 4/1997 | Hackett | A61M 25/09041 | 600/585 |
| 5,624,430 | A | 4/1997 | Eton | | |
| 5,851,185 | A * | 12/1998 | Berns | A61B 17/11 | 600/434 |
| 5,853,375 | A | 12/1998 | Orr | | |
| 5,895,404 | A * | 4/1999 | Ruiz | A61B 17/11 | 600/11 |
| 6,013,038 | A * | 1/2000 | Pflueger | A61M 25/0169 | 600/585 |
| 6,030,334 | A | 2/2000 | Cox | | |
| 6,689,119 | B1 * | 2/2004 | Di Caprio | A61M 25/0127 | 600/585 |
| 6,985,776 | B2 * | 1/2006 | Kane | A61N 1/056 | 600/585 |
| 7,066,924 | B1 | 6/2006 | Garibaldi | | |
| 7,282,057 | B2 * | 10/2007 | Surti | A61B 17/1114 | 606/153 |
| 7,811,294 | B2 | 10/2010 | Strommer | | |
| 7,815,580 | B2 | 10/2010 | Mswanathan | | |
| 8,206,385 | B2 * | 6/2012 | Stangenes | A61B 5/287 | 606/41 |
| 8,295,908 | B2 | 10/2012 | Carmeli | | |
| 8,784,336 | B2 * | 7/2014 | Bown | A61M 25/0127 | 600/585 |
| 9,014,786 | B2 * | 4/2015 | Carmeli | A61B 5/0538 | 601/3 |
| 9,545,263 | B2 * | 1/2017 | Lenihan | A61M 27/002 | |
| 10,028,833 | B2 * | 7/2018 | Spence | A61F 2/2466 | |
| 10,507,302 | B2 * | 12/2019 | Leeflang | A61M 25/0127 | |
| 10,596,356 | B2 * | 3/2020 | Lenihan | A61B 17/3478 | |
| 10,682,070 | B2 * | 6/2020 | Duindam | A61M 25/09 | |
| 10,926,068 | B2 * | 2/2021 | Narayan | A61M 60/865 | |
| 11,052,225 | B2 | 7/2021 | Ryan | | |
| 11,207,503 | B2 * | 12/2021 | Kellerman | A61M 25/09041 | |
| 11,234,722 | B2 * | 2/2022 | Kassab | A61B 17/3478 | |
| 12,017,012 | B2 * | 6/2024 | Akins | A61M 25/0127 | |
| 12,109,347 | B2 * | 10/2024 | Vartanian | A61L 31/022 | |
| 2005/0197557 | A1 * | 9/2005 | Strommer | A61B 34/20 | 600/407 |
| 2006/0079812 | A1 * | 4/2006 | Viswanathan | A61M 25/09 | 600/585 |
| 2007/0265551 | A1 | 11/2007 | Pfister | | |
| 2009/0209900 | A1 * | 8/2009 | Carmeli | A61B 17/22012 | 600/12 |
| 2010/0113919 | A1 * | 5/2010 | Maschke | A61B 17/221 | 606/159 |
| 2010/0145147 | A1 | 6/2010 | Pinsky | | |
| 2012/0089089 | A1 * | 4/2012 | Swain | A61M 25/0127 | 604/95.01 |
| 2013/0226174 | A1 * | 8/2013 | Ibrahim | A61B 18/20 | 606/41 |
| 2015/0196360 | A1 | 7/2015 | Grantham | | |
| 2015/0366580 | A1 * | 12/2015 | Lenihan | A61M 25/0194 | 604/8 |
| 2018/0001056 | A1 * | 1/2018 | Leeflang | A61M 25/0127 | |
| 2018/0133441 | A1 | 5/2018 | Kellerman | | |
| 2018/0333162 | A1 * | 11/2018 | Saab | A61M 25/0108 | |
| 2019/0321606 | A1 * | 10/2019 | Lenihan | A61M 27/002 | |
| 2021/0077787 | A1 | 3/2021 | Ginster | | |
| 2024/0033027 | A1 * | 2/2024 | Perkins | A61B 34/73 | |
| 2024/0277359 | A1 * | 8/2024 | Decker | A61B 90/39 | |
| 2025/0176983 | A1 * | 6/2025 | Owen | A61B 17/22 | |

FOREIGN PATENT DOCUMENTS

| | | | |
|---|---|---|---|
| WO | 2009029869 | A2 | 3/2009 |
| WO | 2010042776 | A2 | 4/2010 |
| WO | 2013108192 | A1 | 7/2013 |
| WO | 2020/117865 | A1 | 6/2020 |
| WO | 2021/087486 | A1 | 5/2021 |

* cited by examiner

Section A-A
86
88
90
84
90
86
88
A
A
82
92
80

MAGNETICALLY DRIVEN CROSSING TOOLS FOR ARTERIAL AND VENOUS OCCLUSIONS

CROSS REFERENCE TO RELATED APPLICATIONS

This application is the U.S. National Phase application under 35 U.S.C. § 371 of International Application No. PCT/EP2022/065265 filed Jun. 3, 2022, which claims the benefit of U.S. Provisional Patent Application No. 63/211,016 filed Jun. 16, 2021. These applications are hereby incorporated by reference herein.

FIELD

The following relates generally to the catheter arts, catheter guidewire arts, vascular therapy arts, and related arts.

BACKGROUND

In catheter-based vascular therapy, a catheter bears one or more tools at its distal end, such as an angioplasty balloon, a laser aperture or cutting tool for thrombectomy or atherectomy, a stent and associated stent deployment hardware, and/or so forth. Initially, a guidewire is inserted into a blood vessel and is fed out until the guidewire crosses past a treatment area (for example, a clot, thrombus, aneurism, or so forth). The catheter has a guidewire lumen and is inserted along the guidewire into the blood vessel to move the catheter tip to the treatment area. However, total (or near total) occlusions within vasculature (e.g., arteries or veins) are very difficult to cross. This may cause the operator (e.g., physician or surgeon) to poke outside of a main lumen of the vessel to get around the occlusion. If the occlusion is able to be crossed, it generally takes an extremely long time in order for a guidewire to slowly push through the blockage. Additionally, the occlusions comprise a stronger material than the vessel wall, meaning that it is easy to cause a rupture in the vessel while attempting to cross the occlusion, which would require additional intervention to fix. Moreover, in some cases, a physician is completely unable to cross the occlusion, which requires a surgical procedure on the occlusion.

The following discloses certain improvements to overcome these problems and others.

SUMMARY

In some embodiments disclosed herein, a guidewire insertion device includes a first guidewire including an electromagnetic tip; a second guidewire including a magnetic tip; and a controller configured to modulate a force of the electromagnetic tip of the first guidewire to control movement of the magnetic tip of the second guidewire.

In some embodiments disclosed herein, a guidewire insertion device includes a guidewire including a ferromagnetic element disposed on or in a tip of the guidewire and an electromagnet disposed on or in the tip of the guidewire; and a controller configured to modulate electric power applied to the electromagnet to produce reciprocating movement of the tip of the guidewire driven by magnetic interaction between the electromagnet and the ferromagnetic element.

In some embodiments disclosed herein, a guidewire insertion device includes a sleeve; a plurality of electromagnets mounted on the sleeve; a guidewire having a ferromagnetic tip; and a controller configured to modulate a force of the electromagnets to control movement of the ferromagnetic tip.

One advantage resides in providing a guidewire insertion device and corresponding guidewire insertion method providing efficient and safe guidewire crossing of a vascular obstruction.

Another advantage resides in providing such a guidewire insertion device and corresponding guidewire insertion method in which the device further includes a second guidewire magnetically engaged with a first guidewire to assist in manipulating the first guidewire to cross a vascular obstruction.

Another advantage resides in providing an electromagnet on a tip of a guidewire to cross a vascular obstruction.

Another advantage resides in providing a guidewire with an electromagnet to ensure that the guidewire does not perforate a wall of a blood vessel.

Another advantage resides in providing a guidewire with an electromagnet to provide an additional force on an end of the guidewire.

Another advantage resides in providing a guidewire with an electromagnet to reduce a time need to cross an occlusion in a blood vessel.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
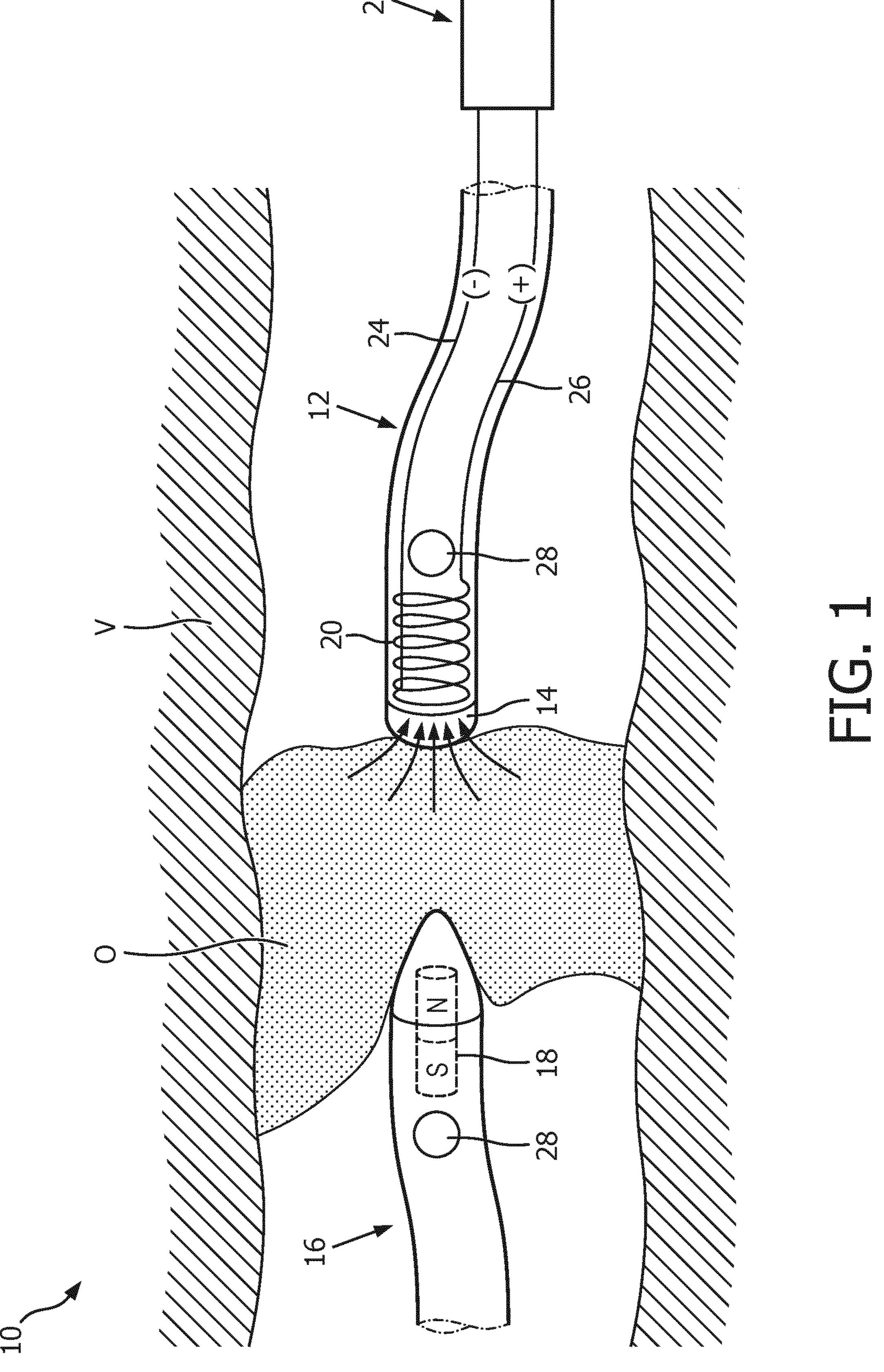
FIG. 1 diagrammatically illustrates a guidewire insertion device in accordance with the present disclosure.

The following discloses various approaches to integrating an electromagnet into the tip of a guidewire to facilitate a crossing of the guide wire through a complete vascular obstruction.

In some embodiments disclosed herein, two guidewires are used, approaching the occlusion from opposite sides. One guidewire has an electromagnet in its tip, and the other has a ferromagnetic tip or a permanent magnet at the tip or another electromagnet. The electromagnet can be energized to attract the tip of the other guidewire toward the electromagnet. Advantageously, the electromagnet can be cycled to modulate this attraction, which can guide the tip and thereby assist the surgeon in pushing the tip of the other guidewire through without perforating the blood vessel wall. If the other guidewire has a permanent magnet or a second electromagnet at its tip, then the force between the two guidewire tips can be modulated between attractive and repulsive, causing the tip of the other catheter to chip away at the occlusion similarly to the operation of a jackhammer. If the other guidewire has a non-magnetized ferromagnetic tip, then this approach can still be used to modulate the attractive force, although a repulsive force is not achievable in this case.

In other embodiments disclosed herein, the guidewire with the electromagnet may further include an expandable cone or funnel. The guidewire includes a deployment sheath that is pulled back to release the cone or funnel. In one approach, the cone or funnel is made of a self-expanding metal such as Nitinol, so it automatically expands when the deployment sheath is pulled back. In another approach, the cone or funnel includes ferromagnetic strips that are magnetized by the electromagnet and repel each other to open the funnel or cone. The purpose of the funnel or cone is to center the electromagnet in the vessel lumen, so that it provides a centered point of attraction for the other guidewire tip. A symmetric cone or funnel facilitates this centering effect. In one possible variant embodiment, once the other guidewire breaks through the occlusion it can contact the electromagnet, so that when the deployment sheath is pressed forward it captures the tip of the other guidewire to form a continuous wire.

In some embodiments disclosed herein, the guidewire has an array of electromagnet coils, e.g., three coils spaced apart radially at 120° intervals. The surgeon can selectively operate the (e.g.) three coils to direct the movement of the other guidewire tip. In another operating mode, if the coils are cycled in polarity a rotational motive force can be created to cause the other guidewire tip to spin, which can facilitate moving it through the occlusion.

The previous embodiments employ two guidewires that approach the occlusion from opposite sides. The following also discloses embodiments suitable for use in cases where only a single guidewire is used.

In one such embodiment, the guidewire has a permanent magnet affixed to its tip, while the electromagnet is loosely fitted inside the guidewire. By cycling the polarity of the electromagnet, the tip can be reciprocated back-and-forth, again providing a jackhammer-type effect to facilitate pushing the tip through the occlusion. In this embodiment the electromagnet may be mounted on a relatively stiff inner wire surrounded by an outer sheath to which the permanent magnet is affixed, so that the electromagnet stays relatively stationary. A variant embodiment puts permanent magnets on both sides of the electromagnet, connected by a nonmagnetic shaft, to provide more balanced reciprocating motion of the assembly.

In yet another embodiment, suitable for use in treating occlusions in a peripheral limb (arm or leg), the guidewire includes a ferromagnetic tip, and an array of electromagnets are mounted on a sleeve that is externally fitted onto the limb. By energizing selected electromagnets of the external encircling array, the direction of movement of the guidewire tip can be biased.

Guidewire insertion is typically performed under image guidance (e.g., fluoroscopy) with the tip(s) of the guidewire(s) marked by radiopaque markers, so the surgeon can visually observe the various movements of the tip(s). After the guidewire crosses the occlusion, a catheter bearing a tool at its distal end (e.g., an angioplasty balloon, a laser aperture or cutting tool for thrombectomy or atherectomy, a stent and associated stent deployment hardware, and/or so forth) may be delivered over the guidewire to remodel, continue to remove, stent, or otherwise treat the occlusion.

With reference to FIG. 1, an illustrative a guidewire insertion device 10 is diagrammatically shown. As shown in FIG. 1, the guidewire insertion device 10 is disposed adjacent an obstruction O within a blood vessel V of a patient. The guidewire insertion device 10 more particularly includes a first guidewire 12 that has an electromagnetic tip 14, and a second guidewire 16 that includes a magnetic tip 18. The magnetic tip 18 of the second guidewire 16 can comprise an electromagnet, a permanent magnet, a ferromagnetic element, or any other suitable magnet. In particular, the illustrative magnetic tip 16 comprises a permanent magnet 18 oriented so that magnetic flux exiting the north pole of the magnet 18 exits the tip of the second guidewire 18. The electromagnetic tip 14 of the first guidewire 12 includes at least one electromagnet 20 (i.e., formed as a solenoid with five illustrative coils (also called turns), more typically including a higher number of turns as the magnetic field of an electromagnet scales with the number of turns. Optionally, the electromagnet 20 may include a ferromagnetic core (not shown) to increase the strength of the magnetic field. The electromagnet 20 is oriented to produce magnetic flux lines exiting or entering the tip of the first guidewire 12. As shown in FIG. 1, the first guidewire 12 is disposed on a first (i.e., "right") side of the occlusion O, and the second guidewire 16 is disposed on a second (i.e., "left") side of the occlusion O. In the illustrative example, the second guidewire 16 has a conical tip to assist in penetrating and crossing the occlusion O. Hence, in the illustrative example it is the catheter tip with the permanent magnet 18 (or, in a variant embodiment, with a ferromagnetic element in its tip) that is expected to cross the occlusion O by moving to the right (in the example of FIG. 1) through the occlusion O in order to cross it. In other embodiments, it is contemplated for the catheter having the electromagnet to be the one that is expected to cross the occlusion.

The guidewire insertion device 10 also includes a controller 22 (e.g., a processor, shown diagrammatically in FIG. 1 as a box) in communication with the first guidewire 12, in particular with the electromagnet 20 of the electromagnetic tip 14. As shown in FIG. 1, the controller 22 is connected to the electromagnetic 20 via a negative pole wire 24 and a positive pole wire 26. The controller 22 is configured to modulate a magnetic force created by the electromagnet 20 of the electromagnetic tip 14 to control movement of the magnetic tip 18 of the second guidewire 16 (e.g., by supplying electric current to the electromagnet 20). That is, when the electromagnetic tip 14 emits a magnetic force, it attracts the magnetic tip 18 of the second guidewire 16 and can therefore control movement of the second guidewire 16. The controller 22 is optionally configured to modulate the magnetic force of the electromagnetic tip 14 of the first guidewire 12 between an attractive force and a repulsive force to control movement of the magnetic tip 18 of the second guidewire 16. The magnetic tip 18 can be controlled with "back and forth movement" produced by modulating the magnetic field generated by the electromagnet 20 to break up the occlusion O with a "jackhammer-type" back-and-forth motion. Because the second guidewire 16 has a permanent magnet 18 at its tip, the magnetic field produced by the electromagnet 20 oscillating between "north-south" and "south-north" by zero crossings of the driving electric current can induce alternating attractive and repulsive force on the permanent magnet 18 for this purpose. If the permanent magnet 18 is replaced by a non-magnetized ferromagnetic slug, then an oscillating magnetic field produced by the electromagnet 20 can induce an oscillation in the attractive force applied to the slug, but cannot induce a repulsive force. Nonetheless, such an oscillation in the attractive force can still assist in breaking up the occlusion O.

In some embodiments, one or more radiopaque markers 28 can be attached to the first guidewire 12 and/or to the second guidewire 16. Advantageously, this can allow the first guidewire 12 and the second guidewire 16 (in particular, the electromagnetic tip 14 and the magnetic tip 18) to be visible under fluoroscopic imaging, thereby allowing a user (e.g., physician, surgeon, or another operator) to visualize the electromagnetic tip 14 and the magnetic tip 18 relative to the occlusion O.

Figure 2:
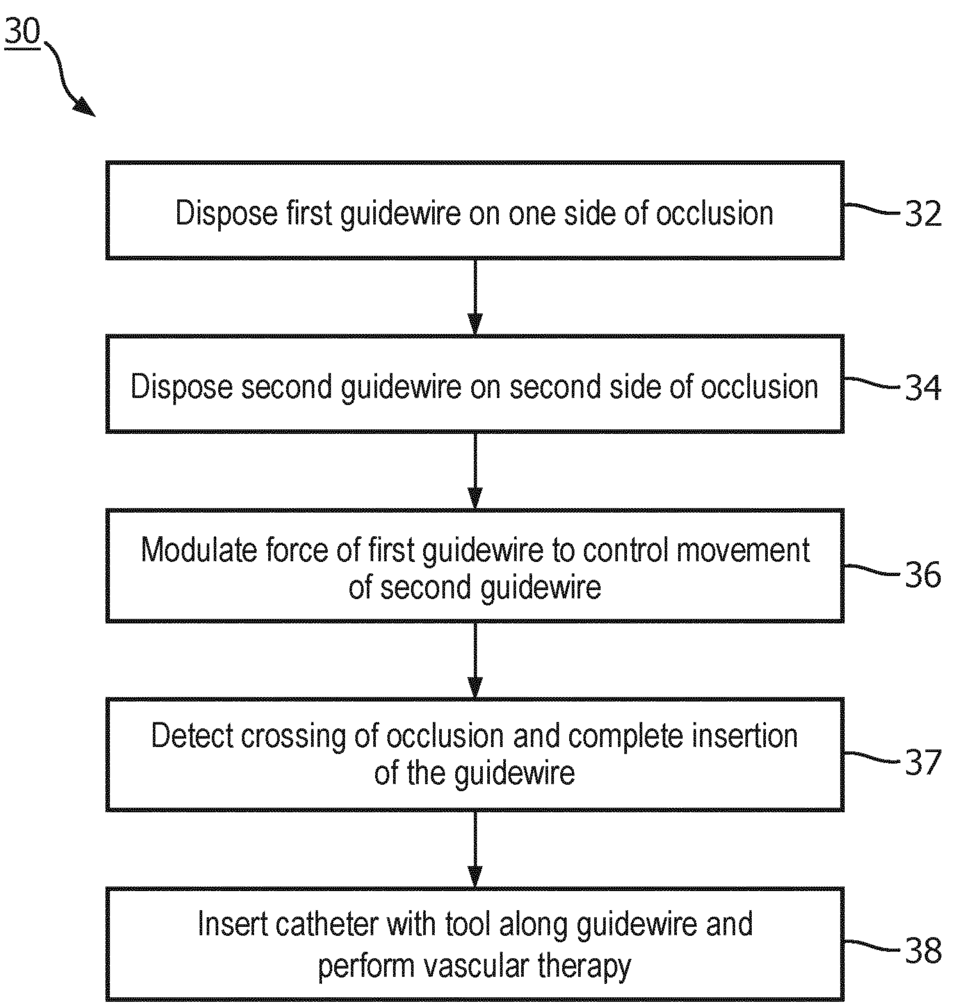
FIG. 2 diagrammatically illustrates a guidewire insertion method suitably performed using the device of FIG. 1.

With continuing reference to FIG. 1, FIG. 2 shows an illustrative embodiment of a vascular therapy method 30 diagrammatically shown as a flowchart. At an operation 32, the first guidewire 12 on a first side of the occlusion O in a target tissue (i.e., the blood vessel V). At an operation 34, the second guidewire 16 is disposed on a second opposing side of the occlusion O. The operations 32, 34 could be reversed in time, or performed concurrently.

At an operation 36, with the tips of the two catheters 12, 16 on opposite sides of the occlusion O, optionally as observed under fluoroscopic imaging, the controller 22 is operated to modulate the force of the electromagnetic tip 14 of the first guidewire 12 to control movement of the magnetic tip 18 of the second guidewire 16. In one example, the controller 22 can be operated to selectively draw the magnetic tip 18 of the second guidewire 16 toward the electromagnetic tip 14 of the first guidewire 12. In another example, the controller 22 can be operated to cycle the force of the electromagnetic tip 14 between a repulsive force and an attractive force to drive a reciprocating motion (i.e., jackhammering motion) of the magnetic tip 18 of the second guidewire 16.

At an operation 37 it is detected that the occlusion has been crossed, for example as observed in fluoroscopic imaging and/or as recognized as the resistance to further insertion of the guidewire 16 abruptly decreases. In another embodiment, crossing may be detected via a sensor (not shown) on the tip of one of the guidewires 12, 16. For example, upon crossing the occlusion O, if the electromagnet 20 is set to attract the magnet 18 of the other guidewire 16 then the two catheter tips may come into direct contact, so that a contact sensor on one or the other of the catheter tips can detect the contact. In another approach, a magnetic sensor on one or the other of the catheter tips can be used to detect close proximity of the magnet 18 of the second guidewire 16 to the electromagnetic tip 14 of the first guidewire 12. With the crossing detected, the operation 37 further includes completion of the insertion of the guidewire 16. For example, it is often desirable to insert the guidewire a certain distance (e.g., a centimeter or a few centimeters) past the therapy location (which is likely to be the occlusion O). In some examples, a physician has created two access points into the vessel V (one for the first guidewire 12 and one for the second guidewire 16). After crossing the occlusion O, one of the guidewires 12, 16 is removed from one of the access points, and the other guidewire 12, 16 is run through the vessel V, and out of the same access site. This gives a physician maximum support for any desired type of catheter for loading over the guidewires 12, 16 for treatment.

With the guidewire insertion complete, a vascular therapy can then be performed in an operation 38 by inserting a catheter with a tool (e.g., angioplasty balloon, laser aperture or cutting tool, stent and associated stent deployment hardware, and/or so forth) along the guidewire and performing vascular therapy using the tool.

Figure 3:
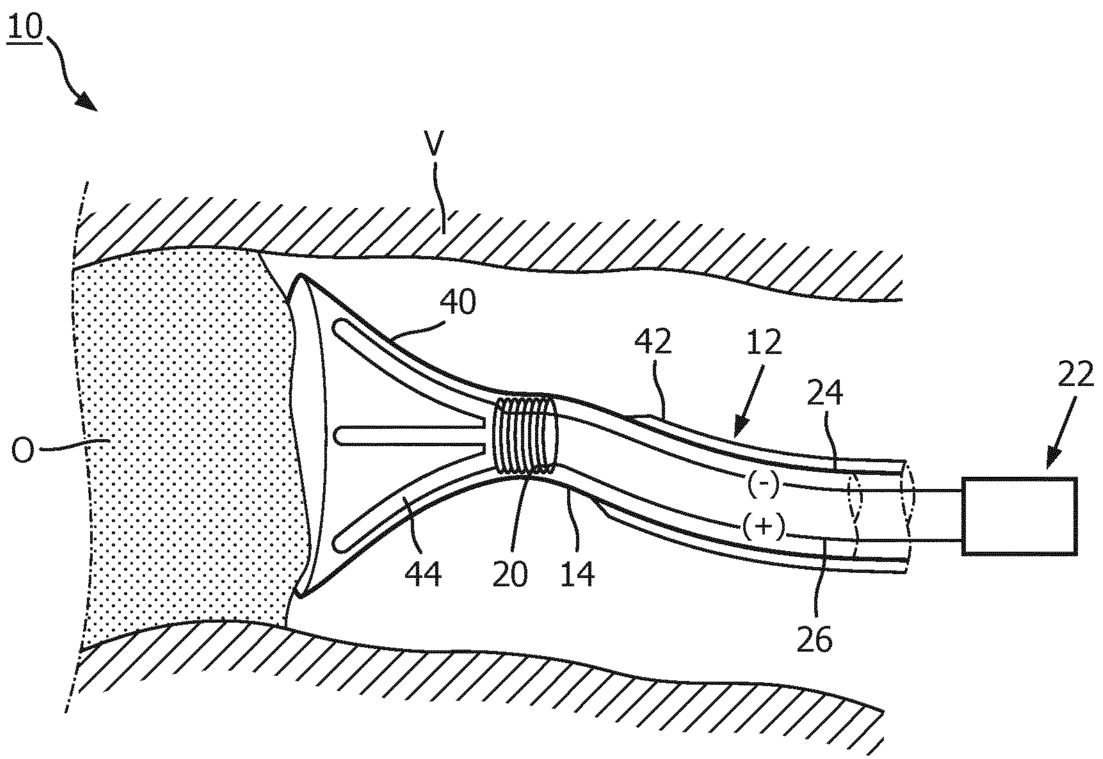
FIG. 3 diagrammatically illustrates a guidewire insertion device according to another embodiment.

FIG. 3 shows another embodiment of the device 10. The embodiment of FIG. 3 includes most of the components of the embodiment of FIG. 1. Notably, the second guidewire 16 is unchanged in the embodiment of FIG. 3 and is therefore not shown. The first guidewire 12 of the embodiment of FIG. 3 again includes the electromagnet 20 and the controller 22 connected with the electromagnet 20 by wires 24, 26. As shown in FIG. 3, the first guidewire 12 includes an expandable member 40 (e.g., having a shape of a cone, a funnel, and so forth) disposed around the electromagnetic tip 14. The expandable member 40 is configured to align the electromagnetic tip 14 in the center of the blood vessel V. This provides a centered position for the electromagnet 20 to thereby center the magnetic tip 18 of the second guidewire 16 (the second guidewire 16 is not shown in FIG. 3 for clarity and brevity) as it is drawn toward the centered electromagnet 20. The expandable member 40 can be a self-expanding member. For example, the expandable member 40 can comprise nitinol in order to be self-expanding. A deployment sheath 42 surrounds the first guidewire 12 and is configured to hold, and subsequently, release the expandable member 40 when the first guidewire 12 is disposed adjacent the occlusion O. In another approach for providing self-expansion of the expandable member 40, the expandable member 40 includes a plurality of ferromagnetic elements 44 (three of which are shown in FIG. 3) that are magnetized by the electromagnetic tip 14 of the first guidewire 12 to cause the ferromagnetic elements 44 to mutually repel to expand the expandable member 40. The expandable member 40 has a magnetic field that tapers as the expandable member approaches the electromagnet 20, thus providing effective centering for the magnetic tip 18 of the other guidewire 16 as it is drawn toward the electromagnet 20. In another contemplated variant (not shown), the expandable member 40 may be replaced by an inflatable balloon (not shown), which is similar to an angioplasty balloon but is inflated to a lower pressure just sufficient to center the electromagnet 20 in the blood vessel V.

Figure 4:
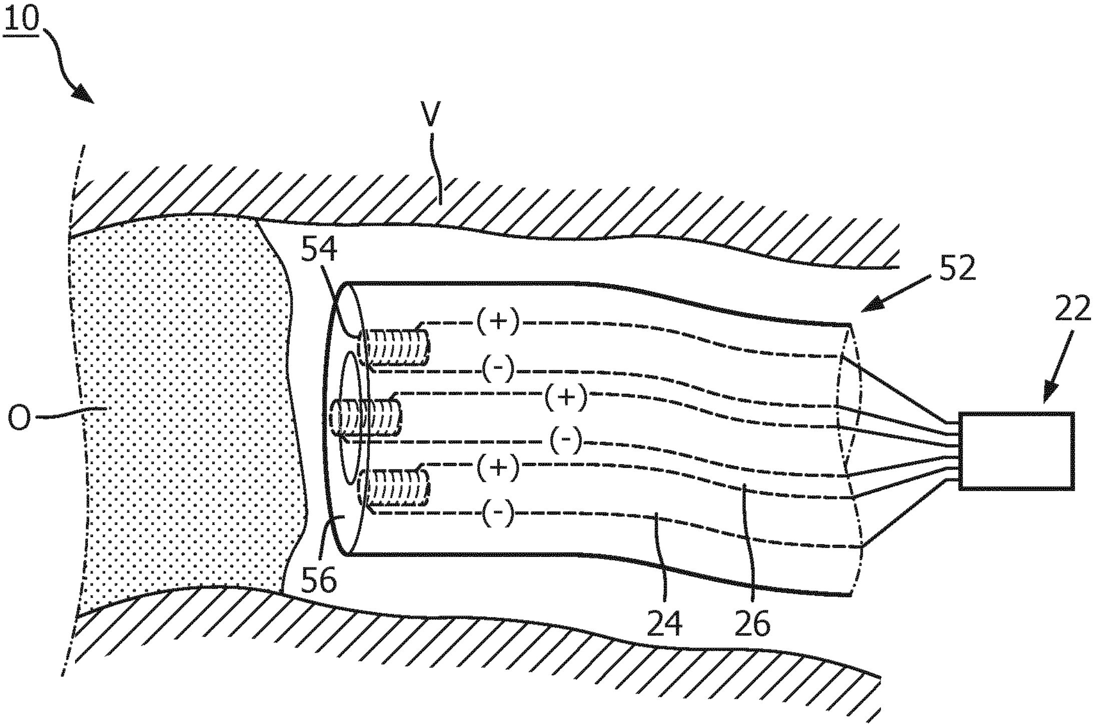
FIG. 4 diagrammatically illustrates a guidewire insertion device according to another embodiment.

FIG. 4 shows an alternative embodiment of the guidewire 20, namely variant guidewire 52, which again is disposed on one side of the occlusion O in the blood vessel V opposite from the other guidewire 16 (not shown in FIG. 4). As shown in FIG. 4, the guidewire 52 includes a plurality of electromagnets 54 (for example, three electromagnets 54 shown in FIG. 4) disposed radially about a tip 56 of the guidewire 52. Each electromagnet 54 is connected to the controller 22 via corresponding negative pole wires 24 and positive pole wires 26, respectively. Each electromagnet 54 is independently operable by the controller 22. This design enables the drawing of the magnet 18 of the other guidewire 16 to be steered by selectively energizing or deenergizing the various electromagnets 54. For example, if the tip of the other guidewire 16 is veering off to the left, then the electromagnet(s) located to the left are turned off and the electromagnet(s) located to the right are turned on to pull the magnet 18 and hence the tip of the guidewire 16 to the right to re-center it. In another example, if the tip of the other guidewire 16 is veering off to the left, then the electromagnet(s) located to the left is switched on so that it repels the top of the guidewire 16, and turn the electromagnet(s) located to the right off (or vice versa).

The illustrative guidewire insertion devices of FIGS. 1, 3, and 4 utilize two guidewires 12, 16 (or two guidewires 52, 16 in the example of FIG. 4) to magnetically assist the crossing of the guidewire 16 through the occlusion O. In the next embodiments described with reference to FIGS. 5, 6, and 7, the guidewire insertion device includes only a single guidewire.

Figure 5:
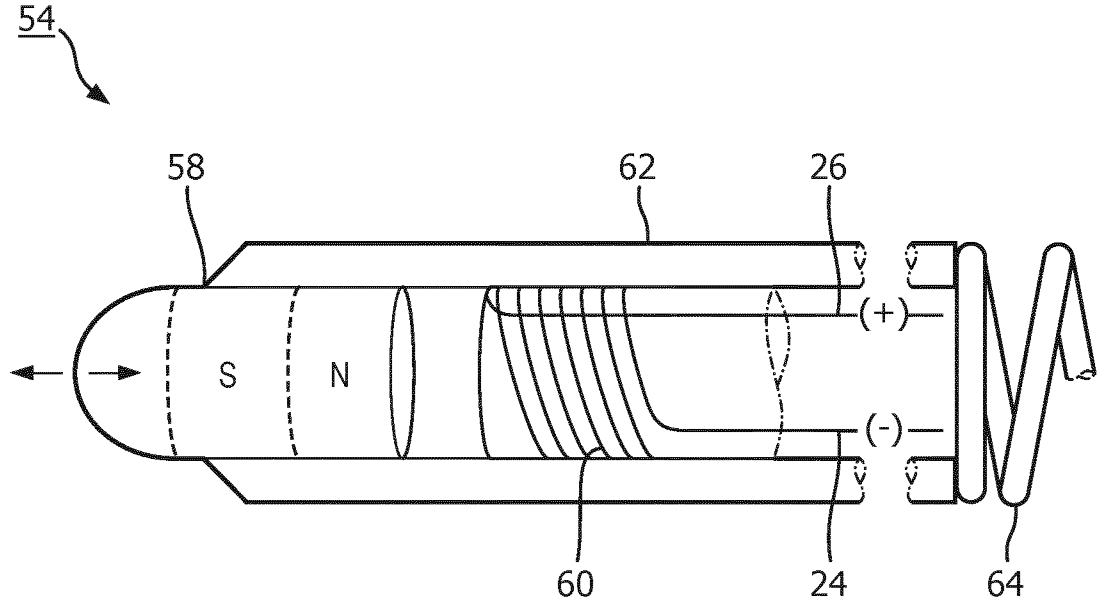
FIG. 5 diagrammatically illustrates a guidewire insertion device according to another embodiment.

With reference to FIG. 5, a guidewire tip 54 includes a ferromagnetic element 58 and an electromagnet 60. For example, the ferromagnetic element 58 is a permanent (i.e., steady-state) magnet, although a non-magnetized ferromagnetic slug is alternatively contemplated. The ferromagnetic element 58 is secured to a sheath 62, and the electromagnet 60 is disposed inside the sheath 62 but is not secured to the sheath 62 (it will be appreciated that an opposing configuration can be implemented, in which the ferromagnetic element 58 is not secured to the sheath 62, and the electromagnet 60 is secured to the sheath 62). A spring 64 is also connected to an end of the sheath 62. The spring 64 allows for movement of the ferromagnetic element 58 relative to the rest of the guidewire.

The controller 22 (not shown in FIG. 5) is configured to modulate electric power applied to the electromagnet 60 to produce reciprocating movement of the guidewire tip 54 driven by magnetic interaction between the electromagnet 60 and the ferromagnetic element 58. The controller 22 supplies current to the electromagnet 60 to draw the ferromagnetic element 58 inward (i.e., away from the occlusion O), which compresses the spring 64. Stopping the current releases the attraction of the ferromagnetic element 58, and the spring 64 will then push the ferromagnetic element 58 outward (i.e., toward the occlusion O). Pulsing current through the electromagnet 60 thus causes the guidewire tip 54 to move back and forth at a frequency equal to the frequency of the pulsing current. This oscillating action can be used to "chip through" the occlusion O. Note that in this embodiment there is only one guidewire.

Figure 6:
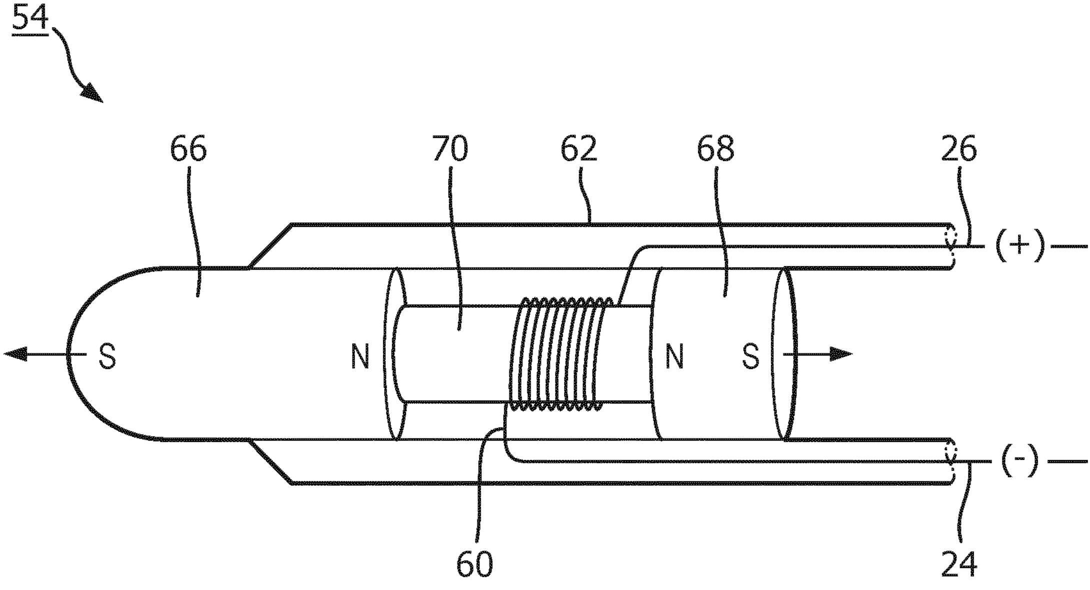
FIG. 6 diagrammatically illustrates a guidewire insertion device according to another embodiment.

With reference to FIG. 6, another embodiment of the guidewire tip 54 is shown. As shown in FIG. 6, the ferromagnetic element 58 includes a first permanent magnet 66 and a second permanent magnet 68, with the electromagnet 60 disposed between the first and second permanent magnets 66, 68. The two permanent magnets 66, 68 are arranged to have the same magnetic pole facing the electromagnet 60. In the illustrative example, the north (N) pole of each magnet 66, 68 faces the electromagnet 20; however, alternatively the south (S) pole of each magnet could be arranged to face the electromagnet 20. The wires 24, 26 are embedded in a wall of the sheath 62 (thereby fixing a position of the electromagnet 60 relative to the sheath 62), while the electromagnet 60, the first magnet 66, and the second magnet 68 are "free-floating" within the sheath 62, but are constrained by physical interference with the electromagnet 60. A non-magnetic shaft 70 is also disposed inside the sheath 62 and connects the two magnets 66, 68, with the turns of the electromagnet 20 disposed around the shaft 70 but not contacting the shaft 70. The first permanent magnet 66 is disposed on a first end of the non-magnetic shaft 70 (e.g., a side adjacent with occlusion O as shown in FIG. 4), and the second permanent magnet 68 is disposed on a second opposing end (e.g., within the sheath 62). The electromagnet 60 is disposed between the first permanent magnet 66 and the second permanent magnet 68. In operation, as the electromagnet 60 is producing a N|S orientation under control of the controller 22 (not shown in FIG. 6), the first magnet 66 is repelled from the facing north pole of the electromagnet 20 while the second magnet 68 is simultaneously attracted to the facing south pole of the electromagnet 20. This urges the assembly including the magnets 66, 68 connected by the shaft 70 forward, i.e., toward the occlusion. When the controller 22 reverses the polarity of the electromagnet 60 to the S|N polarity, the first magnet 66 is attracted to the facing south pole of the electromagnet 20 while the second magnet 68 is simultaneously repelled from the facing north pole of the electromagnet 20. This urges the assembly including the magnets 66, 68 connected by the shaft 70 backward, i.e., away from the occlusion. By cycling the electromagnet 60 between N|S and S|N orientations using the controller 22, the assembly including the magnets 66, 68 connected by the shaft 70 is reciprocated back and forth, providing a "jackhammer" action to assist in crossing the occlusion.

Figure 7:
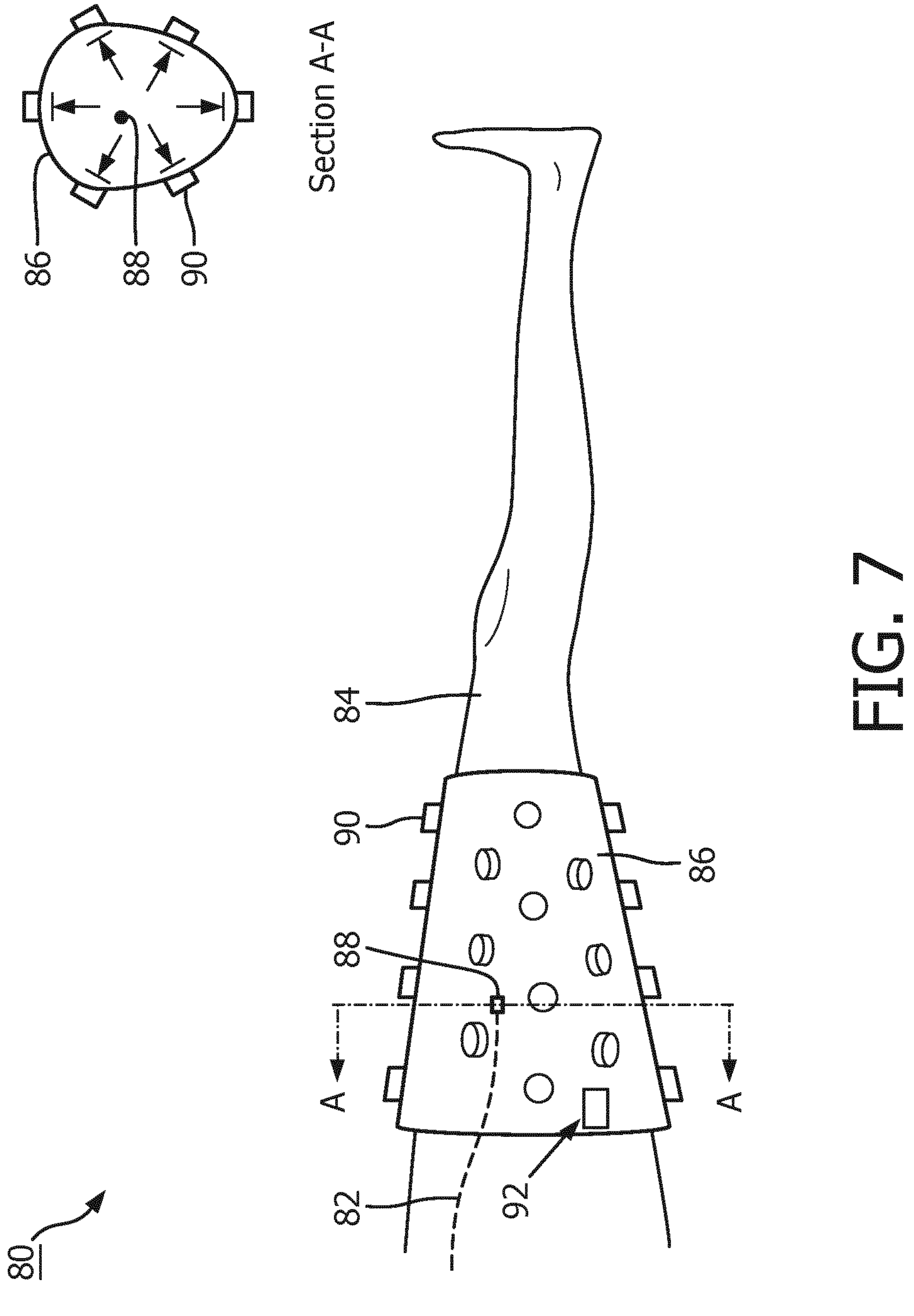
FIG. 7 diagrammatically illustrates a guidewire insertion device according to another embodiment.

FIG. 7 shows another guidewire insertion device 80. As shown in FIG. 7, the device 80 comprises a guidewire 82 that is being inserted into a blood vessel of a patient's limb (illustrative leg) 84, and an external sleeve or cuff 86 configured to be attached to and surround the outside of the limb 84 of the patient (e.g., an arm or illustrative leg). The tip of the guidewire 82 includes a ferromagnetic slug 88, and the sleeve or cuff 86 is positioned externally on the limb 84 around the tip of the guidewire 82. A plurality of electromagnets 90 is mounted on the sleeve 86. A controller 92 operates the electromagnets 90 independently to apply a magnetic force to the magnetic slug 88. As shown in Section A-A of FIG. 7, by energizing selected electromagnets 90 of the encircling array, the direction of movement of the ferromagnetic slug 88, and hence of the tip of the guidewire 82, can be biased toward the energized electromagnet(s). A back-and-forth oscillation of the magnetic slug 88 (and hence of the tip of the guidewire 82) can also optionally be induced by switching the powered electromagnets back and forth. In some examples, due to the number of electromagnets 90 mounted on the sleeve 86, the tip of the guidewire 82 can be moved in any direction in a three-dimensional (3D) space.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A guidewire insertion device, comprising:

a first guidewire including an electromagnetic tip;

a second guidewire including a magnetic tip; and a controller configured to modulate a force of the electromagnetic tip of the first guidewire to control movement of the magnetic tip of the second guidewire.

2. The guidewire insertion device of claim 1, wherein the controller configured to modulate the force of the electromagnetic tip of the first guidewire between an attractive force and a repulsive force to control movement of the magnetic tip of the second guidewire.

3. The guidewire insertion device of claim 1, wherein the magnetic tip of the second guidewire comprises one of an electromagnet, a permanent magnet, or a ferromagnetic element.

4. The guidewire insertion device of claim 1, wherein the electromagnetic tip of the first guidewire includes at least three electromagnets spaced apart radially around a central axis of the first guidewire.

5. The guidewire insertion device of claim 4, wherein the controller is configured to independently modulate the force applied by each respective electromagnet to steer the movement of the magnetic tip of the second guidewire.

6. The guidewire insertion device of claim 1, wherein the first guidewire further includes an expandable member disposed around the electromagnetic tip and configured to align the electromagnetic tip with the magnetic tip of the second guidewire.

7. The guidewire insertion device of claim 6, wherein the expandable member is a self-expanding member, and the first guidewire further includes a deployment sheath configured to release the self-expanding member.

8. The guidewire insertion device of claim 6, wherein the expandable member comprises nitinol.

9. The guidewire insertion device of claim 6, wherein the expandable member includes a plurality of ferromagnetic elements that are magnetized by the electromagnetic tip of the first guidewire to cause the ferromagnetic elements to mutually repel to expand the expandable member.

10. The guidewire insertion device of claim 1, further including one or more radiopaque markers attached to the first guidewire and to the second guidewire.

11. A guidewire insertion method performed using the guidewire insertion device of claim 1, the method comprising:

disposing the first guidewire on a first side of an occlusion in a target tissue;

disposing the second guidewire on a second, opposing side of the occlusion; and operating the controller to modulate the force of the electromagnetic tip of the first guidewire to control movement of the magnetic tip of the second guidewire.

12. The guidewire insertion method of claim 11, wherein the operating includes:

operating the controller to selectively draw the magnetic tip of the second guidewire toward the electromagnetic tip of the first guidewire.

13. The guidewire insertion method of claim 12, wherein the operating includes:

operating the controller to cycle the force of the electromagnetic tip of the first guidewire between a repulsive force and an attractive force to drive a reciprocating motion of the magnetic tip of the second guidewire.

14. A guidewire insertion device, comprising:

a guidewire including a ferromagnetic element disposed on or in a tip of the guidewire and an electromagnet disposed on or in the tip of the guidewire; and a controller configured to modulate electric power applied to the electromagnet to produce reciprocating movement of the tip of the guidewire driven by magnetic interaction between the electromagnet and the ferromagnetic element;

wherein at least the tip of the guidewire is hollow; and further comprising a nonmagnetic shaft disposed inside the hollow tip of the guidewire;

wherein the ferromagnetic element includes first permanent magnet and a second permanent magnet disposed at opposite ends of the nonmagnetic shaft inside the hollow tip of the guidewire.

15. The guidewire insertion device of claim 14, wherein:

at least the tip of the guidewire includes a sheath, and one of ferromagnetic element or the electromagnet is secured to the sheath, and the other of the ferromagnetic element or the electromagnet is not secured to the sheath.

16. The guidewire insertion device of claim 15, wherein the ferromagnetic element is a permanent magnet.

17. The guidewire insertion device of claim 14, wherein the electromagnet is disposed between the first and second permanent magnets and at least one of the first permanent magnet and a second permanent magnet is secured to the guidewire.

* * * * *